(12) United States Patent
Jun et al.

(10) Patent No.: US 8,740,882 B2
(45) Date of Patent: Jun. 3, 2014

(54) MEDICAL ROBOTIC SYSTEM AND METHOD OF CONTROLLING THE SAME

(75) Inventors: Honggul Jun, Seoul (KR); Yoonyoung Chang, Seoul (KR); Woohyun Paik, Seoul (KR)

(73) Assignee: LG Electronics Inc., Seoul (KR)

( * ) Notice: Subject to any disclaimer, the term of this patent is extended or adjusted under 35 U.S.C. 154(b) by 719 days.

(21) Appl. No.: 12/847,269

(22) Filed: Jul. 30, 2010

(65) Prior Publication Data

US 2012/0029529 A1 Feb. 2, 2012

(51) Int. Cl.
*A61B 19/00* (2006.01)
(52) U.S. Cl.
USPC ............................................... 606/1; 606/130
(58) Field of Classification Search
USPC ........... 901/9–10, 14–18, 33; 128/898; 606/1, 606/130
See application file for complete search history.

(56) References Cited

U.S. PATENT DOCUMENTS

| | | | |
|---|---|---|---|
| 6,356,807 B1 * | 3/2002 | McGee et al. | 700/253 |
| 6,493,608 B1 * | 12/2002 | Niemeyer | 700/302 |
| 7,395,606 B2 * | 7/2008 | Crampton | 33/503 |
| 2003/0125716 A1 | 7/2003 | Wang et al. | |
| 2004/0106916 A1 * | 6/2004 | Quaid et al. | 606/1 |
| 2006/0041249 A1 * | 2/2006 | Niemeyer | 606/1 |
| 2007/0021870 A1 * | 1/2007 | Nagasaka | 700/245 |
| 2007/0287992 A1 * | 12/2007 | Diolaiti et al. | 606/1 |
| 2008/0221391 A1 | 9/2008 | Weitzner et al. | |
| 2008/0258670 A1 * | 10/2008 | Yoshikawa | 318/568.22 |
| 2009/0105878 A1 * | 4/2009 | Nagasaka | 700/245 |
| 2009/0248037 A1 * | 10/2009 | Prisco | 606/130 |

* cited by examiner

*Primary Examiner* — Bill Thomson
*Assistant Examiner* — Jeffrey Lipitz
(74) *Attorney, Agent, or Firm* — Birch, Stewart, Kolasch & Birch, LLP

(57) ABSTRACT

A medical robotic system and method for controlling the system are provided to precisely measure contact force during the minimally invasive surgery. In one embodiment, a medical robotic system includes an input device, a robotic arm assembly, a surgical instrument operably coupled to the robotic arm assembly, the surgical instrument including a contact detection unit configured to detect a contact of the surgical instrument with tissue of a patient, a current measurement unit configured to measure a joint current in the robotic arm assembly, a position/velocity measurement unit configured to measure a joint position and a joint velocity in the robotic arm assembly, an external force calculation unit configured to calculate size and direction of a contact force caused by the contact of the surgical instrument to the tissue based on the joint currents, positions and velocities measured when the contact is occurred and measured when the contact is not occurred.

9 Claims, 12 Drawing Sheets

MEDICAL ROBOTIC SYSTEM AND METHOD OF CONTROLLING THE SAME

BACKGROUND OF THE INVENTION

1. Field of the Invention

The present invention relates a medical robotic system and a method of controlling medical robotic system and in particular, relates to a force-reflecting medical robotic system and a method of controlling the system.

2. Discussion of the Related Art

Minimally invasive surgery can reduce the amount of extraneous tissue which must be damaged during diagnostic or surgical procedures in comparison with a conventional open surgery, thereby reducing patient recovery time, discomfort, and deleterious side effects. In addition, the minimally invasive manner can minimize the trauma due to surgical procedures. Thus, the number of surgical procedures using the minimally invasive manner is gradually increasing in various medical fields such as general surgery, urology, gynecology, and cardio surgery.

However, there are also many disadvantages of current minimally invasive surgical technology. In essence, during conventional open surgeries, the tips of the various instruments may be positioned with six degrees of freedom. However, by inserting an instrument through a small aperture, such as one made in a patient to effectuate a minimally invasive procedure, two degrees of freedom are lost. It is this loss of freedom of movement within the surgical site that has substantially limited the types of minimally invasive surgery procedures that are performed.

In addition, the instruments pivot at the point (i.e. fulcrum) where they penetrate the body wall causing the tip of the instrument to move in opposite direction to the surgeon's hand.

Minimally invasive procedures are conducted by inserting surgical instruments and an endoscope through small incision in the skin of the patient. Manipulating such instruments can be awkward. It has been found that a high level of dexterity is required to accurately control the instruments. Additionally, human hands typically have at least a minimal amount of tremor. The tremor further increases the difficulty of performing minimally invasive cardiac procedures. The length and construction of instruments reduces the surgeon's ability to feel force exerted by tissues and organs on the end effector of the tool.

In order to overcome these disadvantages, techniques adapting robots to the minimally invasive surgery have been rapidly developed since 1990s. For example, teleportation techniques used in a conventional nuclear power plant and space development were utilized so as to develop these surgical robots. The system using such surgical robots enables to provide the surgeon with visual depth perception by adapting 3D stereo vision technique to a laparoscope. The system also enables to provide the surgeon with feeling as if manipulating the surgical instruments directly by his/her hand. Especially, the system enables the surgeon to perform more accurate procedures by enlarging the image while reducing the movement of the instruments.

The robotic surgery adapts coordinates transformation and position estimation techniques, like this. However, proposed methods of performing telesurgery create many new challenges. One of the challenges is transmitting force from the surgical instrument back to the surgeon's hands such that the surgeon can feel resistance to movements of the instruments when the instrument contacts tissue.

The force-reflecting control technique utilizes a Lorentz force actuator where an input current is output as a torque of a joint. This technique can be used if the status of a robot is recognized by measuring the angular velocities and the angles of the joints, and this technique embodies the force-reflection by transmitting a force to a master, which is proportional to a slave's position displacement due to a repulsive force. However, it is necessary for this technique to compensate components associated with friction, rotor inertia and structural vibration in a real motor in order to be more widely used.

Methods using a macro-micro system for overcoming such problem were developed, and these methods are disclosed in documents such as U.S. Pat. No. 5,807,377 and U.S. patent publication No. 2005/0073718 A1. The methods divide the whole system into a macro system and a micro system, thus reduce the inertia and friction of the micro system and improve the structural vibration characteristics, thereby utilize the system as a means for measuring forces. In addition, the system allows a wide range of motion of the surgical instrument by the macro system which includes multiple joints robot and also allows high positioning accuracy. The system is currently adapted to a few of the surgical robots however it is not widely used because of problems such as time delay.

Other various techniques which directly measures forces and transmit the forces to the master have been developed as another method for the force-reflecting control. These techniques may be divided into two different types, and the first type is a method for measuring torques by directly connecting torque sensors to actuators. The document, Paul, B. J., "A system approach to the torque control of a permanent magnet brushless motor," Technical report, MIT Artificial Intelligent Laboratory, AI-TR 1081 (1987), suggested that this method can remove the effects of friction or rotor inertia. This method is disclosed in the document, Korean patent publication No. 10-2010-0075229.

The second method is to use force sensors attached at end effectors, and the document, Mason, M. and Salisbury, J. K., "Robot Hand and the Mechanics of Manipulation," MIT Press (1985), suggested that this method can remove the effects of friction, rotor inertial and structural vibration characteristics. This method is disclosed in the document, U.S. patent publication No. 2007/0151391 A1. A method using a force/torque sensor attached at a trocar needle is also disclosed in the document, Korean patent publication No. 10-2007-0037565.

However, these methods have the following disadvantages. First, the method using torque sensors attached to actuators can induce additional position errors due to the means of measuring torque. Second, in the method using sensor attached to end effectors, it is necessary to induce a transformation of a link portion so as to increase sensitivity of the sensor, and this may deteriorate the position accuracy. The method also induces additional expenses for the surgical instruments. Third, the method using a sensor attached to a trocar needle may induce malfunction when the trocar needle is detached from the incision during the surgical procedure. Forth, the method using a sensor attached to ends of the instrument may induce problems in the expenses, sterilization and shielding EMI.

As functions of the terminal are diversified, the terminal is implemented as a multimedia player provided with composite functions such as photographing of photos or moving pictures, playback of music or moving picture files, game play, broadcast reception and the like for example.

To support and increase of the terminal functions, it may be able to consider the improvement of structural part and/or software part of the terminal.

Generally, a broadcast receiving terminal outputs a broadcast content in a manner of receiving broadcast relevant information provided by a broadcast provider and then outputting the broadcast content using the received broadcast relevant information.

In case of attempting to control a broadcast output operation, a broadcast receiving terminal receives an input of a command signal for controlling a broadcast output from a user and then performs a control operation corresponding to the inputted control command signal.

However, according to the related art, a control action for a broadcast output operation can be inputted in a manner of manipulating the broadcast receiving terminal itself. Moreover, when a control action is inputted using a small mobile terminal, a user may have difficulty in inputting the corresponding control action.

SUMMARY OF THE INVENTION

Thus, it is an object of the present invention to provide a medical robotic system and control method for precisely measuring the force during the minimally invasive surgery.

It is also an object of the present invention to provide a medical robotic system and control method for improving the time delay characteristics.

It is also an object of the present invention to provide a medical robotic system and control method for preventing deterioration of positioning accuracy.

It is also an object of the present invention to provide a medial robotic system and control method for measuring the force during the minimally invasive surgery without generating additional expenses, sterilization, and EMI problems.

A medical robotic system and a method for controlling the system are provided to precisely measure contact force during the minimally invasive surgery. In one embodiment, a medical robotic system includes an input device, a robotic arm assembly, a surgical instrument operably coupled to the robotic arm assembly, the surgical instrument including a contact detection unit configured to detect a contact of the surgical instrument with tissue of a patient, a current measurement unit configured to measure a joint current in the robotic arm assembly, a position/velocity measurement unit configured to measure a joint position and a joint velocity in the robotic arm assembly, an external force calculation unit configured to calculate size and direction of a contact force caused by the contact of the surgical instrument to the tissue based on the joint currents, the joint positions and the joint velocities measured when the contact is occurred and measured when the contact is not occurred.

The external force calculation unit may include an output unit configured to receive a contact signal from the contact detection unit, output the contact force when the contact is occurred, and output a reference value for the contact force when the contact is not occurred.

The external force calculation unit may include a coordinate calculation unit configured to receive the joint position and the joint velocity from the position/velocity measurement unit and convert the joint position and the joint velocity into a Cartesian position and a Cartesian velocity respectively, a joint motor simulation unit configured to receive the joint current from the current measurement unit and convert the joint current into a joint torque signal, and a force/moment calculation unit configured to receive the joint torque signal from the joint motor simulation unit, receive the Cartesian position and the Cartesian velocity from the coordinate calculation unit, and generate Cartesian force/moment of the contact force based on the joint torque signal and the Cartesian position/velocity.

The joint motor simulation unit may include a motor model configured to calculate a time domain response of the joint torque signal considering rotor inertia and friction of a joint motor.

The motor model may be represented by the following formula:

$$\text{Torque} = JM\frac{d^2 i}{dt^2} + KM(i) - sat(vel/\eta)FM,$$

where "JM" is a rotor inertia constant, "KM" is a current/torque conversion constant, "vel" is a joint velocity, "$\eta$" is a chattering removal margin, "sat( )" is a saturation function, and "FM" is a friction constant.

The joint motor simulation unit further includes a slave inverse dynamics unit configured to receive the joint position and the joint velocity from the position/velocity measurement unit, receive the Cartesian force/moment as a feedback signal, and compute torque components generated by friction and inertia of the joint motor based on the joint position, the joint velocity and the Cartesian force/moment when the contact is not occurred, and a parameter learning unit configured to store the current/torque conversion constant, the rotor inertia constant and the friction constant when the contact is not occurred.

The surgical instrument may have an end effector including the contact detection unit, and the contact detection unit is located at the end effector and configured to detect a contact between the end effector and the tissue.

The contact detection unit may be configured to detect the contact between the end effector and the tissue by measuring a leakage current generated when the contact is occurred.

The contact detection unit may be configured to detect the contact between the end effector and the tissue by measuring discharge induced by the contact.

The contact measurement unit may include a plurality of separate electrodes located respective portions of the end effector such that a portion of the end effector at which a contact is occurred can be determined. The input device may be configured to receive the contact force.

In another embodiment, a method of controlling a medical robotic system includes determining whether the surgical instrument is contacted with tissue of a patient, measuring a joint velocity, a joint position and a joint current when the surgical instrument is not contacted with the tissue, measuring a joint velocity, a joint position and a joint current when the surgical instrument is contacted with the tissue, calculating size and direction of a contact force caused by the contact of the surgical instrument with the tissue based on the joint positions, the joint velocities, and the joint currents measured when the contact is occurred and when the contact is not occurred, and transmitting the contact force to the input device.

The method may further include outputting a reference force value for the contact force when the contact is not occurred.

The calculating size and direction of the contact force may includes converting the joint position and the joint velocity into a Cartesian position and a Cartesian velocity respectively, converting the joint current into a joint torque signal, and generating Cartesian force/moment of the contact force based on the joint torque signal and the Cartesian position and the Cartesian velocity.

The converting the joint current into a joint torque signal may include calculating a time domain response of the joint torque signal considering rotor inertia and friction of a joint motor by using a motor model, where the motor model may be represented by the following formula:

$$\text{Torque} = JM\frac{d^2 i}{dt^2} + KM(i) - sat(vel/\eta)FM,$$

where "JM" is a rotor inertia constant, "KM" is a current/torque conversion constant, "vel" is a joint velocity, "η" is a chattering removal margin, "sat( )" is a saturation function, and "FM" is a friction constant.

The converting the joint current into a joint torque signal may further include computing torque components generated by friction and inertia based on the joint position, the joint velocity and the Cartesian force/moment when the contact is not occurred, and storing the current/torque conversion constant, the rotor inertia constant and the friction constant when the contact is not occurred.

The present invention provides a medical robotic system and control method which can precisely measure the force during the minimally invasive surgery and reflect the measured fore to a surgeon's hand such that the surgeon is able to perform a more intuitive surgery.

The present invention also provides a medical robotic system and control method which improve the time delay characteristics by detecting a contact.

The present invention also provides a medical robotic system and control method which can prevent deterioration of positioning accuracy because the system does not require any additional sensors or the like.

BRIEF DESCRIPTION OF THE DRAWINGS

The accompanying drawings, which are included to provide a further understanding of the invention, illustrate embodiments of the invention and together with the description serve to explain the principle of the invention.

DETAILED DESCRIPTION OF THE INVENTION

Reference will now be made in detail to the preferred embodiments of the present invention, examples of which are illustrated in the accompanying drawings.

Exemplary embodiments described hereinafter are combinations of elements and features of the present invention. The elements or features may be considered selective unless otherwise mentioned. Each element or feature may be practiced without being combined with other elements or features. Further, an embodiment of the present invention may be constructed by combining parts of the elements and/or features. Operation orders described in embodiments of the present invention may be rearranged. Some constructions of any one embodiment may be included in another embodiment and may be replaced with corresponding constructions of another embodiment.

To simplify the description herein and in the claims, the term "joint" is to be understood as a connection (translational or revolute) between two links, and may include gears as well as any other controllable component coupled to linear drive mechanisms that may be used in controlling robotic arm assemblies.

Figure 1:
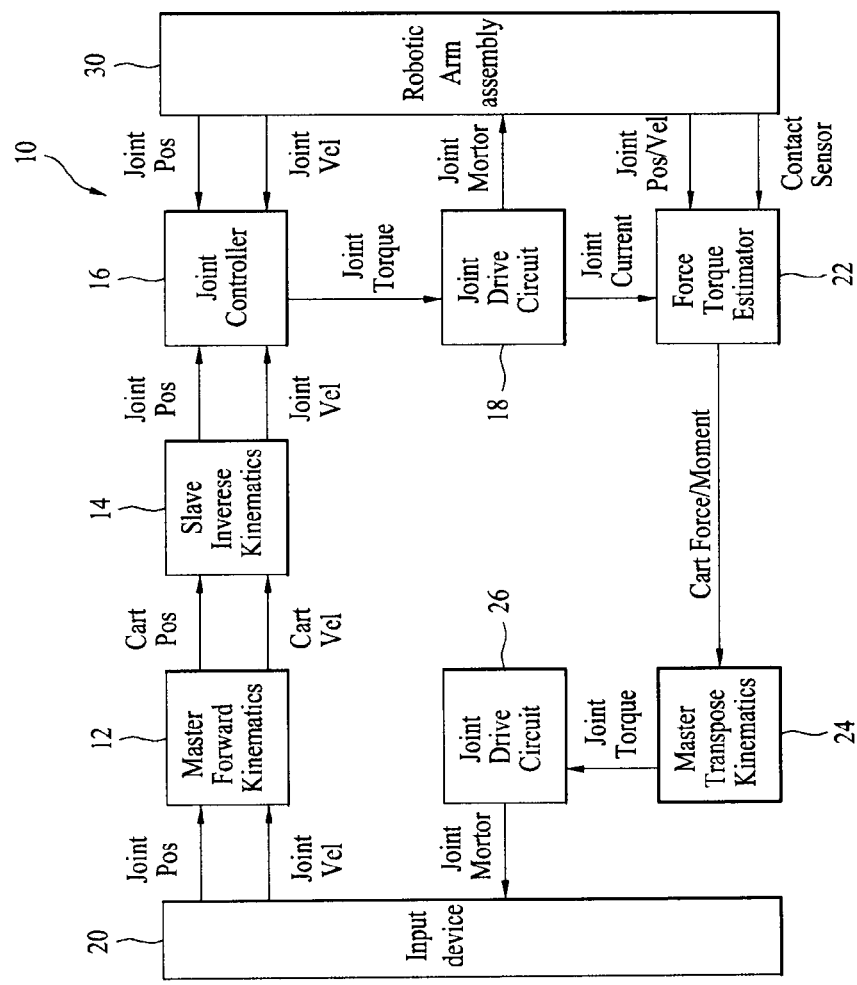
FIG. 1 is a block diagram illustrating a medical robotic system according to an exemplary embodiment of the present invention.

FIG. 1 illustrates a block diagram of a medical robotic system according to an exemplary embodiment of the present invention. A surgeon manipulates a robot arm assembly 30 including a plurality of joints by using an input device 20 that is a master of the system so as to perform a surgery. The system embodies a force-reflecting control which transmits the contact force due to a contact between tissues or organs and a surgical instrument to the input device 20. The system makes use of currents applied to joint motors to measure the force applied to the end effector of the surgical instrument.

As shown in FIG. 1, the medical robotic system includes a processor 10 for controlling movement of the robotic arm assembly 30 and consequently, the position and orientation of its attached surgical instrument, as commanded by movement of the input device 20 by a surgeon.

Both the input device 20 and the robotic arm assembly 30 include a number of linkages connected by joints so as to facilitate multiple degrees-of-freedom movement. As the surgeon moves the input device 20 from one position to another during the course of performing a surgical procedure, sensors associated with the input device joints provide information indicating such command movement in master joint space, and sensors associated with the robotic arm assembly joints provide information indicating robotic arm assembly and consequently, surgical instrument movement in slave joint space for feedback purposes.

A master forward kinematics processing unit 12 receives master joint positions and velocities from the input device 20 and transforms them into Cartesian positions and velocities, using, for example, a Jacobian matrix. For economy of words, Cartesian position is to be interpreted to include Cartesian orientation in this specification where appropriate.

A slave inverse kinematics processing unit 14 receives the Cartesian positions and velocities from the master forward kinematics processing unit 12 and transforms them into slave joint positions and velocities.

A joint control unit 16 receives the slave joint positions and velocities from the slave inverse kinematics processing unit 14 and generates slave joint torque signals for the slave joint motors. The joint control unit 16 also receives slave joint positions and velocities from the robotic arm assembly as feedback signals.

A slave joint drive circuit unit 18 receives the slave joint torque signals from the joint control unit, generates electric currents corresponding to the slave joint torque signals, and supplies the electric currents to the corresponding slave joint motors in the robotic arm assembly 30. The slave joint drive circuit unit 18 also measures slave joint currents. That is, the slave joint drive circuit unit 18 includes a current measurement unit.

For example, the current measurement unit may measure the current by monitoring a current feedback signal of a drive circuit of a DC brush motor. As another example, in case of a brushless DC (BLDC) motor, the current measurement unit may also measure the current by monitoring a current feedback signal, where the current feedback signal is generated by removing phase sinusoidal components from a current signal for driving the motor, and the current signal is output from a drive circuit where the current signal is synchronized with a sinusoidal phase output signal for improving electrical cogging characteristics.

Figure 2:
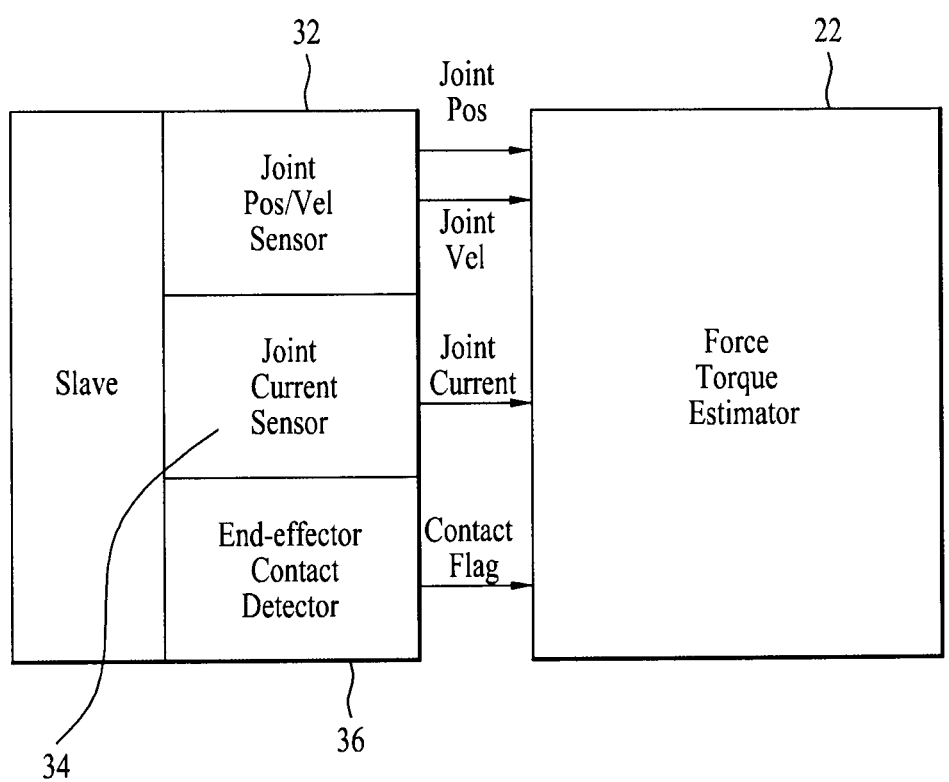
FIG. 2 is a block diagram illustrating sensors and a contact detector according to the exemplary embodiment of the present invention.

An external force calculation unit 22 receives the slave joint currents from the joint drive circuit unit 18 (i.e. the current measurement unit 34 of FIG. 2), receives the slave joint positions (i.e. angles) and velocities (i.e. angular velocities) from the robotic arm assembly 30 (i.e. a position/velocity measurement unit 32 of FIG. 2) and receives a contact signal from the robotic arm assembly 30 (i.e. a contact detection unit 36 of FIG. 2). The external force calculation unit 22 calculate size and direction of a contact force caused by the contact of the surgical instrument to tissues or organs based on the slave joint currents, positions and velocities measured when the contact is occurred and measured when the contact is not occurred, where the contact force may be a Cartesian force/movement as shown in FIG. 1. However, the present invention is not limited to this, and the external force calculation unit 22 may also output the contact force in a joint space. Further details for the external force calculation unit 22 will be described in reference to FIG. 2 and FIG. 3

A master transpose kinematics processing unit 24 receives the Cartesian force/movement from the external force calculation unit 22 and generates a corresponding torque signal in joint space using, for example, the Jacobian transpose matrix and kinematics relationships associated with the input device 20.

A master joint drive circuit unit 26 receives the master torque signals from the master transpose kinematics processing unit 24, generates electric currents corresponding to the master torque signals, and supplies the electrical currents to corresponding master joint motors in the input device 20. As a result, a surgeon operating the input device 20 feels the Cartesian force/moment when the surgeon instruments and the tissue are contacted with each other.

FIG. 2 illustrates a block diagram of sensors and a contact detection unit according to the exemplary embodiment of the present invention. As shown in FIG. 2, the medical robotic system includes a contact detection unit 36 for detecting a contact of the surgical instrument with tissue of a patient, a current measurement unit 34 for measuring a joint current in the robotic arm assembly 30, a position/velocity measurement unit 32 for measuring a joint position and a joint velocity in the robotic arm assembly 30, and the external force calculation unit 22 for calculating size and direction of a contact force caused by the contact of the surgical instrument to the tissue based on the joint currents, the joint positions and the joint velocities measured when the contact is occurred and measured when the contact is not occurred.

The contact detection unit 36 may be located at an end effector of the surgical instrument. Thus, in this case, the contact detection unit 36 detects a contact between the end effector and the tissue. The contact detection unit 36, for example, may detect the contact between the end effector and the tissue by measuring a leakage current generated when the contact is occurred (FIG. 7), and also for another example, the contact detection unit 36 may detect the contact by measuring discharge induced by the contact (FIG. 8). In addition, the contact measurement unit 36 may include a plurality of separate electrodes located respective portions of the end effector such that a portion of the end effector at which a contact is occurred can be discriminated (FIG. 9).

The signals output from the contact detection unit 36 may include high frequency distortion due to various noises, thereby the contact detection unit 36 may maintain the signals as contact status when a contact is once detected even though the signals are distorted during a certain period of time, and then the contact detection unit 36 may initialize the period of the maintenance when a contact is detected again.

As described above, the current measurement unit 34 may be located at the slave joint drive circuit unit 18. For example, the position/velocity measurement unit 32 may measure the joint positions (i.e. angles) and the joint velocities (i.e. angular velocities) by using an incremental encoder. The incremental encoder may be attached to an axis of a slave joint motor, its value is initialized at a predetermined position, and the joint positions are measured by the change of the value of the encoder with respect to the initialized value. The joint velocities are calculated by measuring the change of the value during a predetermined time interval.

As another example, the position/velocity measurement unit 32 may measure the joint positions and velocities by using an analog potentiometer of which resistance is changed according to the rotation angle of the motor and a tachometer of which voltage is changed according to the velocity of the rotation. The joint positions are measured by supplying a reference voltage to the analog potentiometer and detecting the output voltage according to the change of the resistance. The joint velocities are measured by detecting the output voltage of the tachometer.

The external force calculation unit 22 may calculate Cartesian force/moment of the contact force from the difference of the joint current, position, and velocity measured when the contact is occurred and the joint current, position, and velocity measured when the contact is not occurred.

Figure 3:
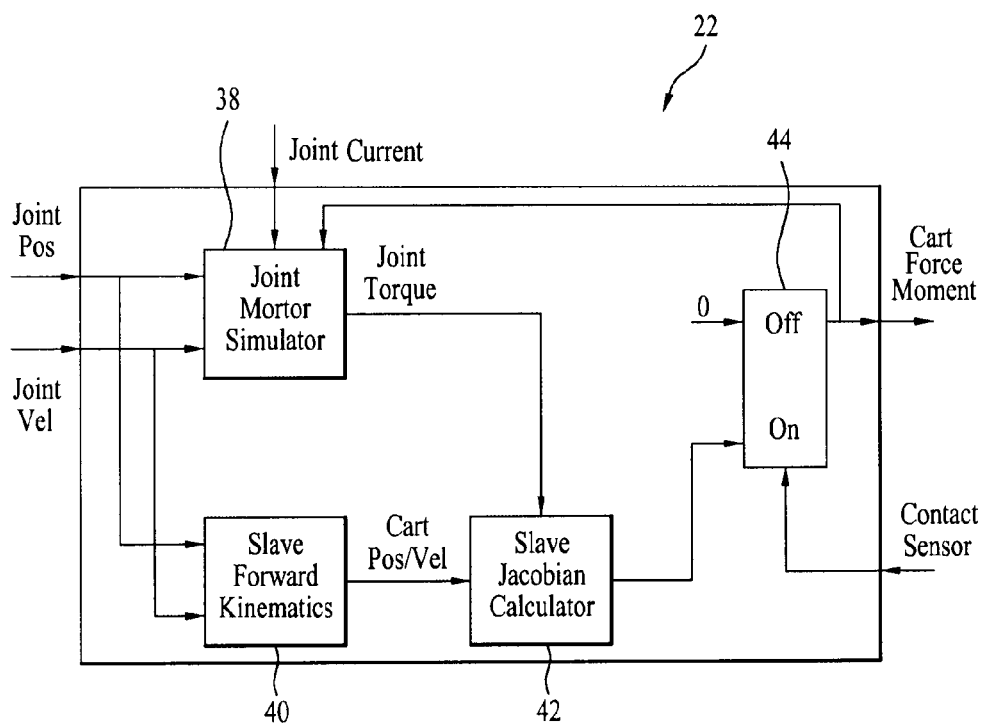
FIG. 3 is a block diagram illustrating an external force calculation unit of the medical robotic system.

FIG. 3 illustrates a block diagram of the external force calculation unit 22. As shown in FIG. 3, the external force calculation unit 22 includes a coordinate calculation unit 40, a joint motor simulation unit 38, a force/moment calculation unit 42, and an output unit 44.

The coordinate calculation unit 40 receives the joint position and the joint velocity from the position/velocity measurement unit 32 and converts the joint position and velocity in a joint space into a Cartesian position and a Cartesian velocity respectively in a Cartesian space which is set up based on a screen (i.e. obtained through a laparoscope).

The joint motor simulation unit 38 receives the joint current from the current measurement unit 34 and converts the joint current into a joint torque signal. More details of the joint motor simulation unit 38 will be described in reference to FIG. 4.

The force/moment calculation unit 42 receives the joint torque signal from the joint motor simulation unit 38, receives the Cartesian position and the Cartesian velocity from the coordinate calculation unit 40, and generates Cartesian force/moment of the contact force based on the joint torque signal and the Cartesian position/velocity, using, for example, a Jacobian matrix.

The output unit 44 receives a contact signal from the contact detection unit, outputs the contact force when the contact is occurred, and outputs a reference value (i.e. zero value) for the contact force when the contact is not occurred.

Figure 4:
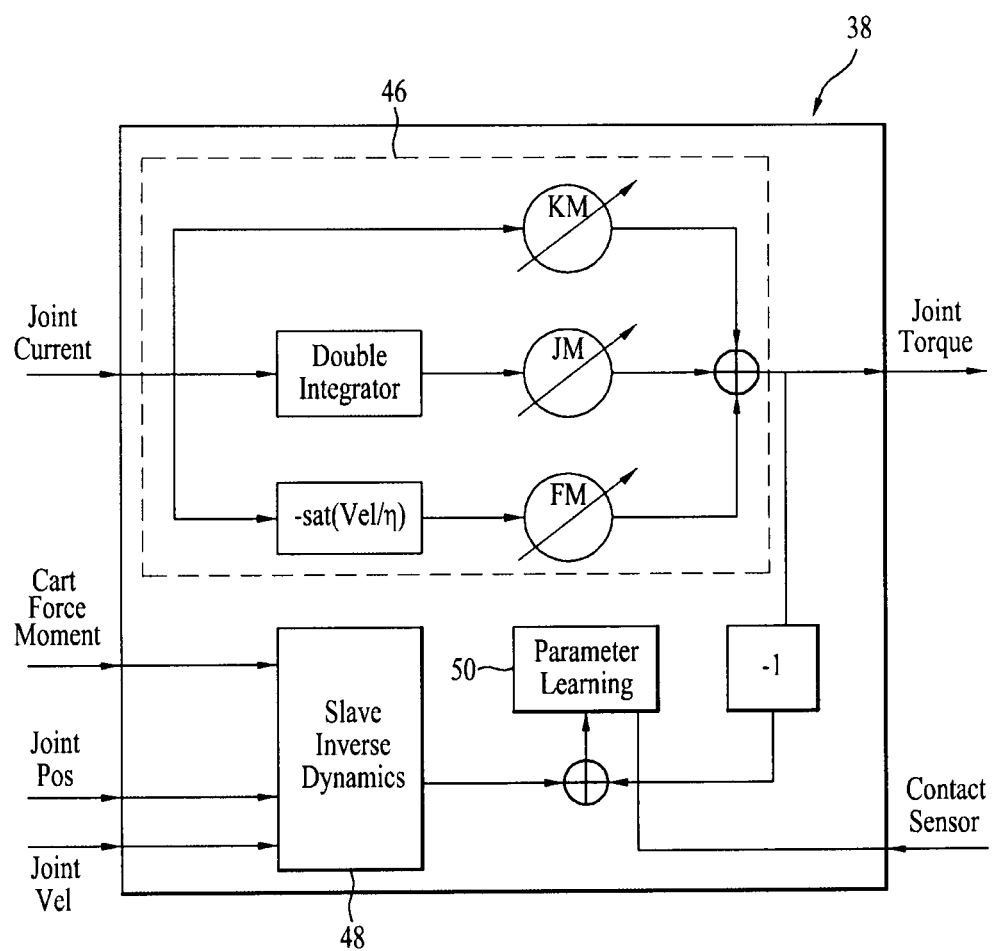
FIG. 4 is a block diagram illustrating a joint motor simulation unit of the external force calculation unit.

FIG. 4 illustrates a block diagram of the joint motor simulation unit 38. As shown in FIG. 4, the joint motor simulation unit 38 includes a slave inverse dynamics unit 48, a motor model 46, and a parameter learning unit 50.

The motor model 46 calculates a time domain response of the joint torque signal considering rotor inertia and friction of the joint motor, where the motor model may be represented by the following formula:

$$\text{Torque} = JM\frac{d^2 i}{dt^2} + KM(i) - sat(vel/\eta)FM$$

where "JM" is a rotor inertia constant, "KM" is a current/torque conversion constant, "vel" is a joint velocity, "$\eta$" is a chattering removal margin, "sat( )" is a saturation function, and "FM" is a friction constant.

The slave inverse dynamics unit 48 receives the joint position and the joint velocity from the position/velocity measurement unit 32, receives the Cartesian force/moment from the force/moment calculation unit 42 as a feedback signal, and computes torque components generated by friction and inertia of the joint motor based on the joint position, the joint velocity and the Cartesian force/moment measured when the contact is not occurred. In this case, the tools and joints of the end effector may have much lower inertia than that of the joint motor, thus the slave inverse dynamics unit 48 may be represented as a simplified constant.

A parameter learning unit 50 stores the current/torque conversion constant, the rotor inertia constant and the friction constant when the contact is not occurred. Initial values of the constants of the motor model which are obtained from additional experiments may be stored in a memory, and the parameter learning unit may only learn constants within certain ranges from the initial values in order to improve the stabilization of the learning.

Figure 5:
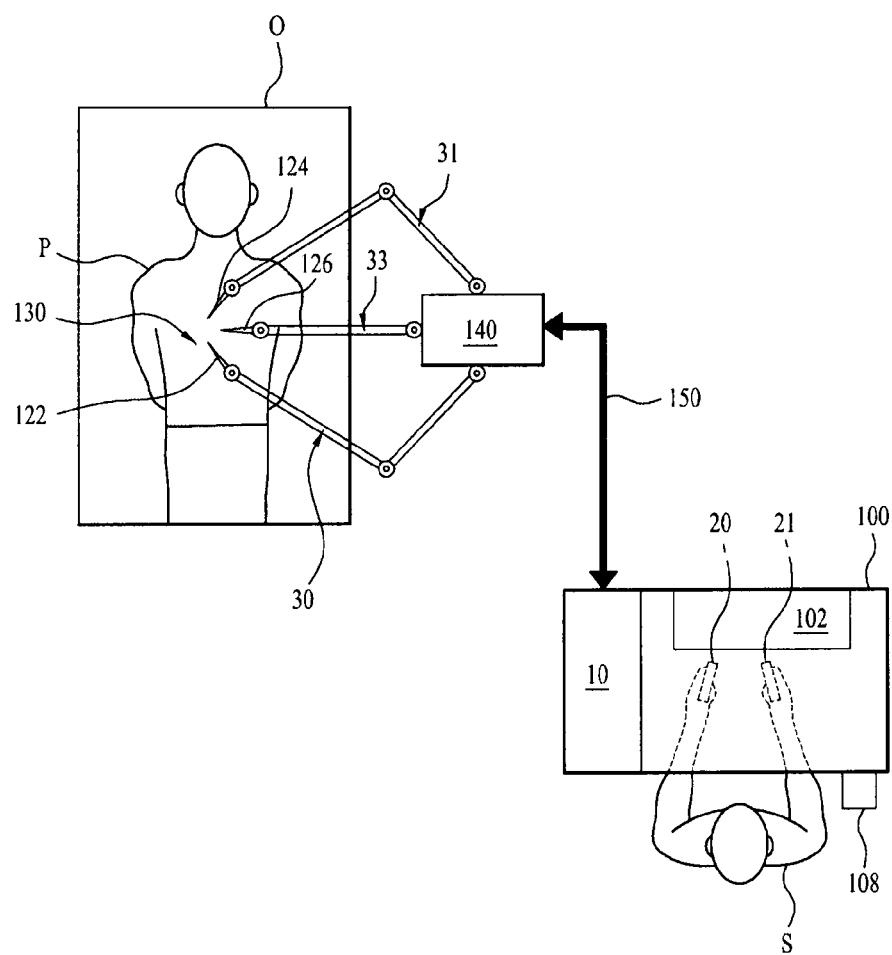
FIG. 5 is a top view illustrating the medical robotic system.

FIG. 5 illustrates, as an example, a top view of an operating room employing a medical robotic system according to an exemplary embodiment of the present invention. The medical robotic system is a minimally invasive robotic surgical system including a console 100 utilized by a surgeon (S) while performing a medical procedure, such as a diagnostic or surgical procedure on a patient (P) who is reclining on an Operating table (O).

The console 100 includes a 3-D monitor 102 for displaying a 3-D image of a surgical site to the surgeon, left and right manipulatable input devices 20, 21, a foot pedal 108, and a processor 10. The input devices 20, 21 may include any one or more of a variety of input devices such as joysticks, gloves, trigger-guns, hand-operated controllers, or the like. The processor 10 may be a dedicated computer integrated into the console 100 or positioned next or near to it, or it may be broken up into a number of processing or controller components that are distributed in a distributed processing fashion throughout the system.

The surgeon performs a medical procedure by manipulating the input devices 20, 21 so that the processor 10 causes slave manipulators of their respectively associated robotic arm assemblies 30, 31 to manipulate their respective removably coupled surgical instruments 122, 124 accordingly, while the surgeon views the surgical site in 3-D on the console 100 monitor 102 as it is captured by a stereoscopic endoscope 126.

Each of the surgical instruments 122, 124, as well as the endoscope 126, is conventionally inserted through a tool guide into the patient so as to extend down to the surgical site through a corresponding minimally invasive incision such as incision 130. The number of surgical tools used at one time and consequently, the number of robotic arms being used in the system will generally depend on the medical procedure being performed and the space constraints within the operating room, among other factors. If it is necessary to change a tool being used during a procedure, the Assistant may remove the tool no longer being used from its robotic arm assembly, and replace it with other surgical instruments.

Each of the robotic arm assemblies 30, 31, 33 includes a robotic arm assembly and setup arms. The slave manipulators are robotically moved using motor controlled joints in order to manipulate and/or move their respectively held medical devices and their end effectors. The setup arms may be manually manipulated by releasing normally braked joints to horizontal and vertical positions of the robotic arm assemblies 30, 31, 33 so that their respective medical devices may be inserted into their respective tool guides. The robotic arm assemblies 30, 31, 33 are mounted on a structure 140 which may be a patient-side cart or a ceiling mount.

Preferably, the monitor 102 is positioned near the surgeon's hands so that it will display a projected image that is oriented so that the surgeon feels that he or she is actually looking directly down onto the operating site. To that end, images of the surgical instruments 122, 124 preferably appear to be located substantially where the surgeon's hands are located.

The processor 10 performs various functions in the system. One important function that it performs is to translate and transfer the mechanical motion of input devices 20, 21 to their respective slave manipulators of robotic arm assemblies 30, 31 through control signals over bus 150 so that the surgeon can effectively manipulate their respective surgical instruments 122, 124. Another important function is to implement various control system processes and the methods as described herein. Although described as a processor, it is to be appreciated that the processor 10 may be implemented in practice by any combination of hardware, software and firmware. Also, its functions as described herein may be performed by one unit, or divided up among different components, each of which may be implemented in turn by any combination of hardware, software and firmware.

Figure 6:
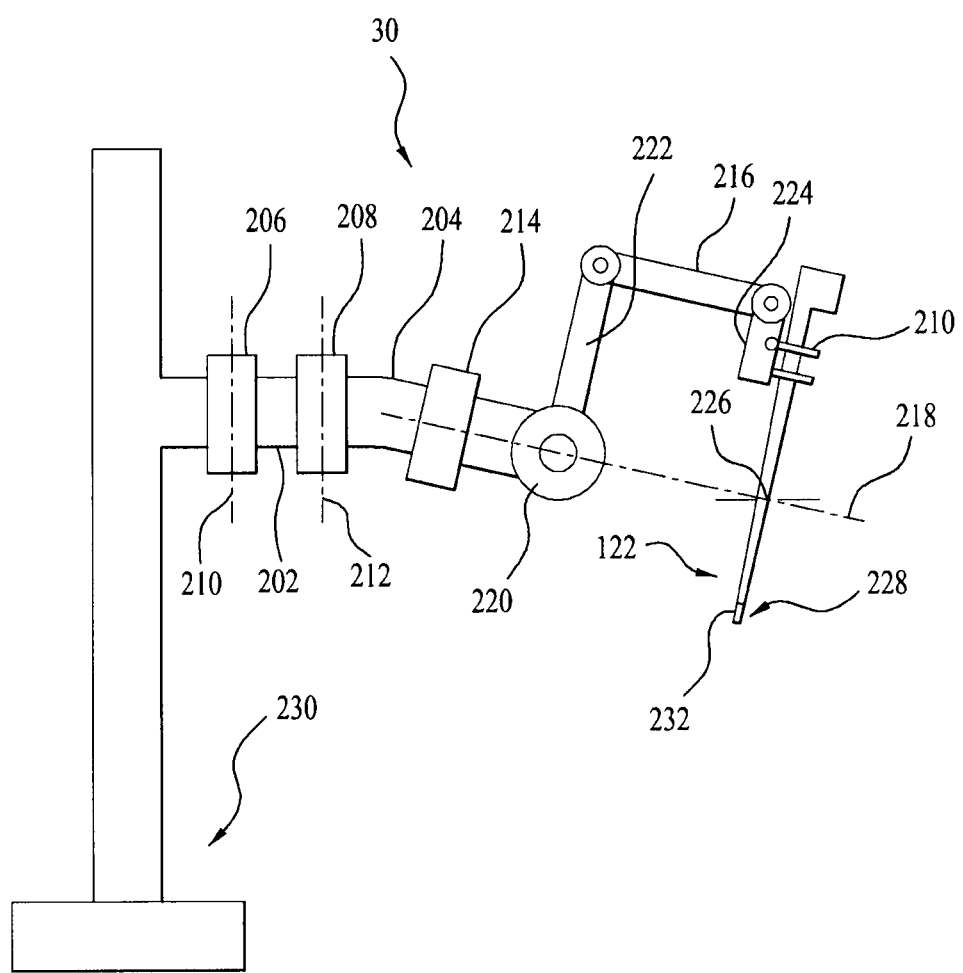
FIG. 6 is a side view illustrating a robotic arm assembly of the medical robotic system.

FIG. 6 illustrates, as an example, a side view of a simplified (not necessarily in proportion or complete) version of the robotic arm assembly 30 (which is also representative of the robotic arm assemblies 31, 33) holding the surgical instrument 122 for performing a medical procedure. A tool guide 210 is inserted through the minimally invasive incision 130 in the patient, and coupled to the robotic arm assembly 30 by a guide holder 220. The surgical instrument 122 may then be inserted into the patient through the tool guide 210. The robotic arm assembly 30 is mechanically supported by a base 230, which may be part of a patient-side movable cart 140.

Links 202, 204 are coupled together and to the base 230 through horizontal setup joints 206, 208. The setup joints 206, 208 in this example are passive joints that allow manual positioning of the arm 30 when their brakes are released. For example, setup joint 206 allows link 202 to be manually rotated about axis 210, and setup joint 208 allows link 204 to be manually rotated about axis 212. This portion of the robotic arm assembly 30 including these passive joints is referred to herein as the setup arm.

Although only two links and two setup joints are shown in this example, more or less of each may be used as appropriate in this and other robotic arm assemblies in conjunction with the present invention. For example, although setup joints 206, 208 are useful for horizontal positioning of the arm 30, additional setup joints may be included and useful for limited vertical and angular positioning of the arm 30. For major vertical positioning of the arm 30, however, the arm 30 may also be slidably moved along the vertical axis of the base 230 and locked in position.

The robotic arm assembly 30 also includes two active joints and a number of gears driven by motors. A yaw joint 214 allows arm section 216 to rotate around an axis 218, and a pitch joint 220 allows arm section 216 to rotate about an axis perpendicular to that of axis 218 and orthogonal to the plane of the drawing. The portion of the robotic arm assembly 30 including these active joints and motor driven gears is referred to herein as the slave manipulator.

The arm section 216 is configured so that sections 222, 224 are always parallel to each other as the pitch joint 220 is rotated by its motor. As a consequence, the instrument 122 may be controllably moved by driving the yaw and pitch motors so as to pivot about the pivot point 226, which is generally located through positioning of the setup joints 206, 208 so as to be at the point of entry into the patient.

Although each of the yaw joint 214, pitch joint 220 and motor driven gears in the carriage 228 is controlled by an individual joint or gear controller, the controllers may be controlled by a common processor 10 so that the robotic arm assembly of the robotic arm assembly 30 may be controlled through user (i.e. surgeon or operator) manipulation of its associated input device. A contact detection unit 36 is provided to detect a contact between tissue of the patient and the end effector 228.

Figure 7:
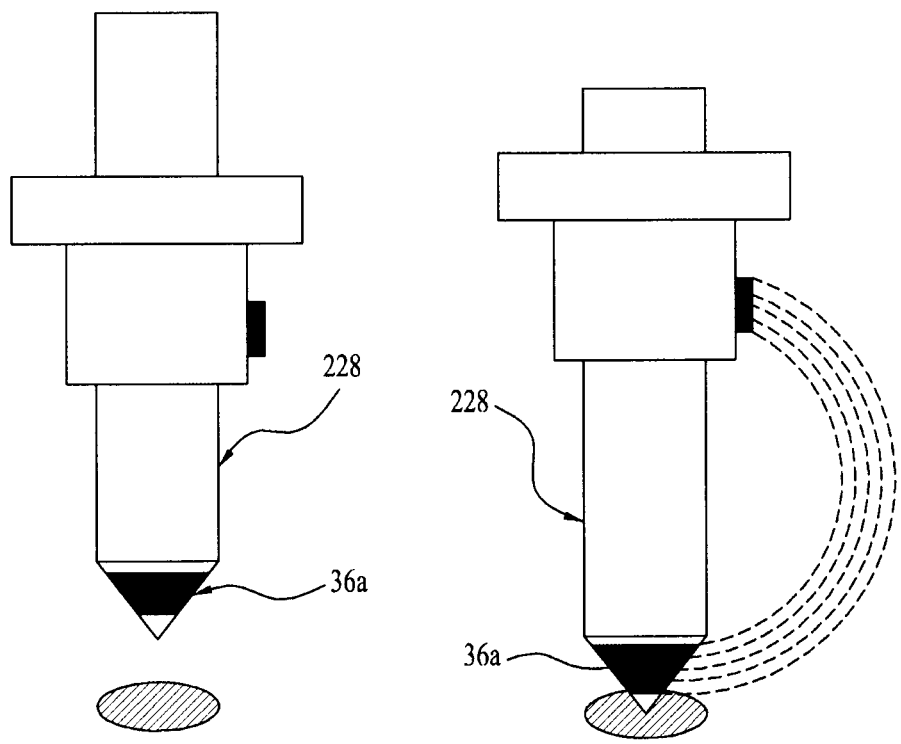
FIG. 7 to FIG. 9 are schematic views illustrating end effectors according to exemplary embodiments of the present invention.
Figure 8:
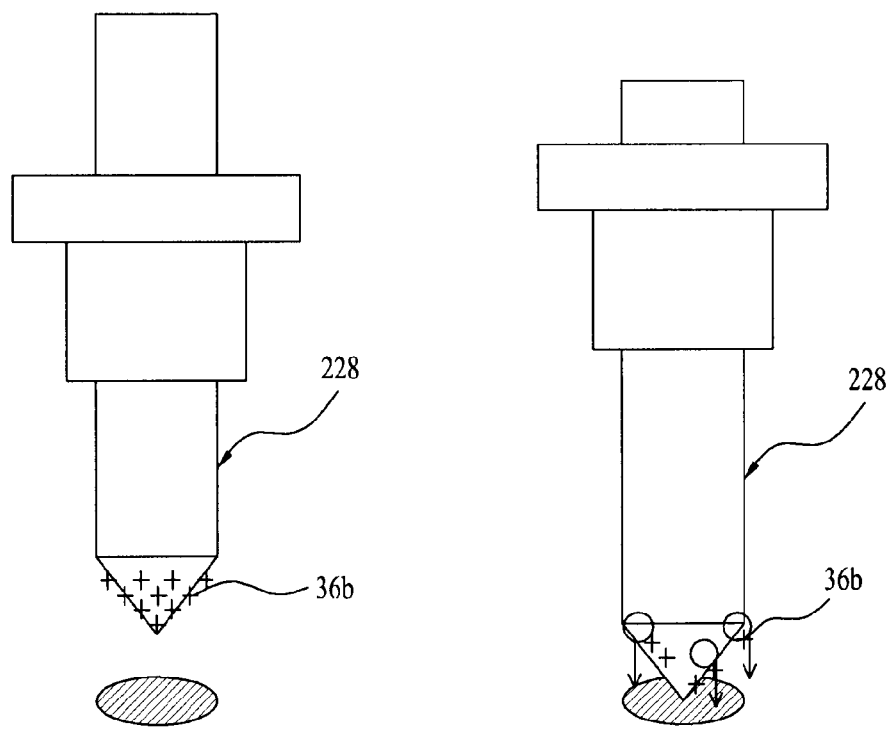
Figure 9:
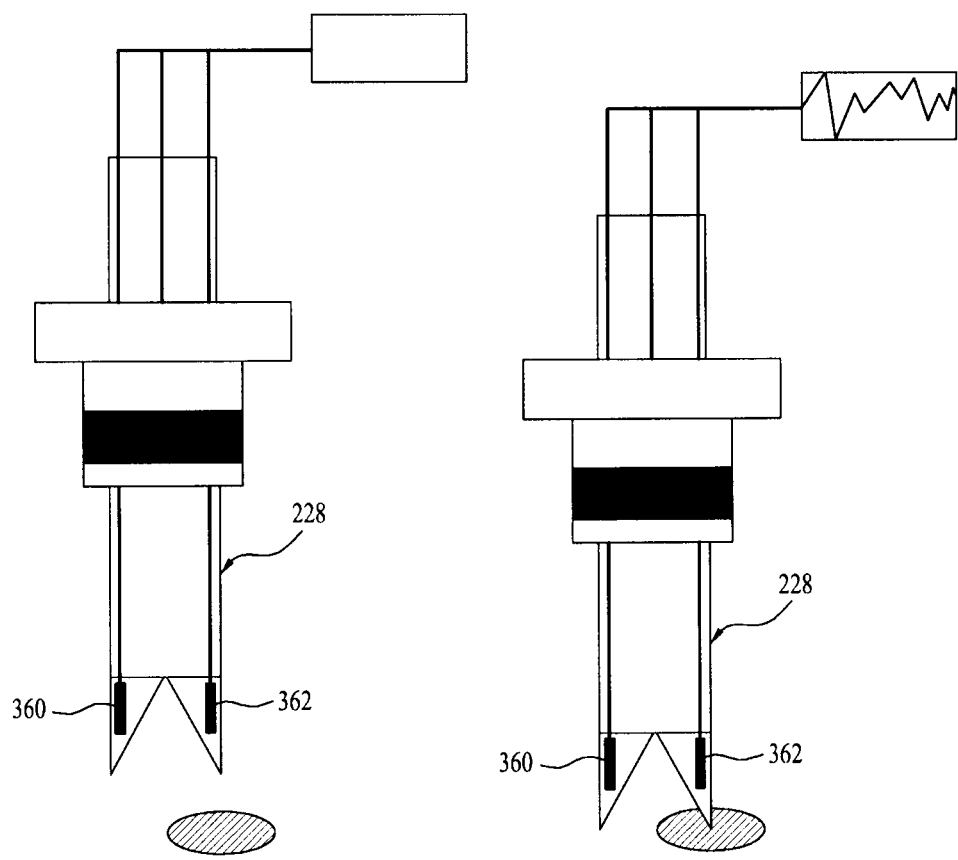

FIGS. 7 to 9 illustrate schematic views of examples of the end effectors 228 having contact detection units. Hereinafter, examples of the contact detection unit will be described in reference to the drawings.

FIG. 7 shows the end effector 228 having a contact detection unit 36a of a leakage current detection type. In this example, a voltage signal of a predetermined frequency is applied between an electrode located at an end of the end effector 228 and an electrode located at a contact portion at which the tissue is to be contacted during the surgical procedure and thus, the contact detection unit 36a determines whether the contact is occurred by detecting a leakage current generated by the contact.

FIG. 8 shows the end effector 228 having a contact detection unit 36b of a discharge detection type. In this example, an end of the end effector is electrically charged, and then the contact detection unit determines whether the contact is occurred by detecting discharge generated by the contact.

FIG. 9 shows another example of the contact detection unit which having a plurality of electrodes 360, 362 separate from each other at respective portions of the end effector. It is possible for the contact detection unit of this example to discriminate which portion of the end effector among the portions where the electrodes 360, 362 are located is contacted to the tissue by this example of the contact detection unit. This example may be adapted to the examples of FIG. 7 and FIG. 8 thus, the contact detection unit may be a leakage current detection type or also may be a discharge detection type.

A method of controlling a medical robotic system according to an exemplary embodiment of the present invention will be described hereinafter in reference to FIG. 10 to FIG. 12.

Figure 10:
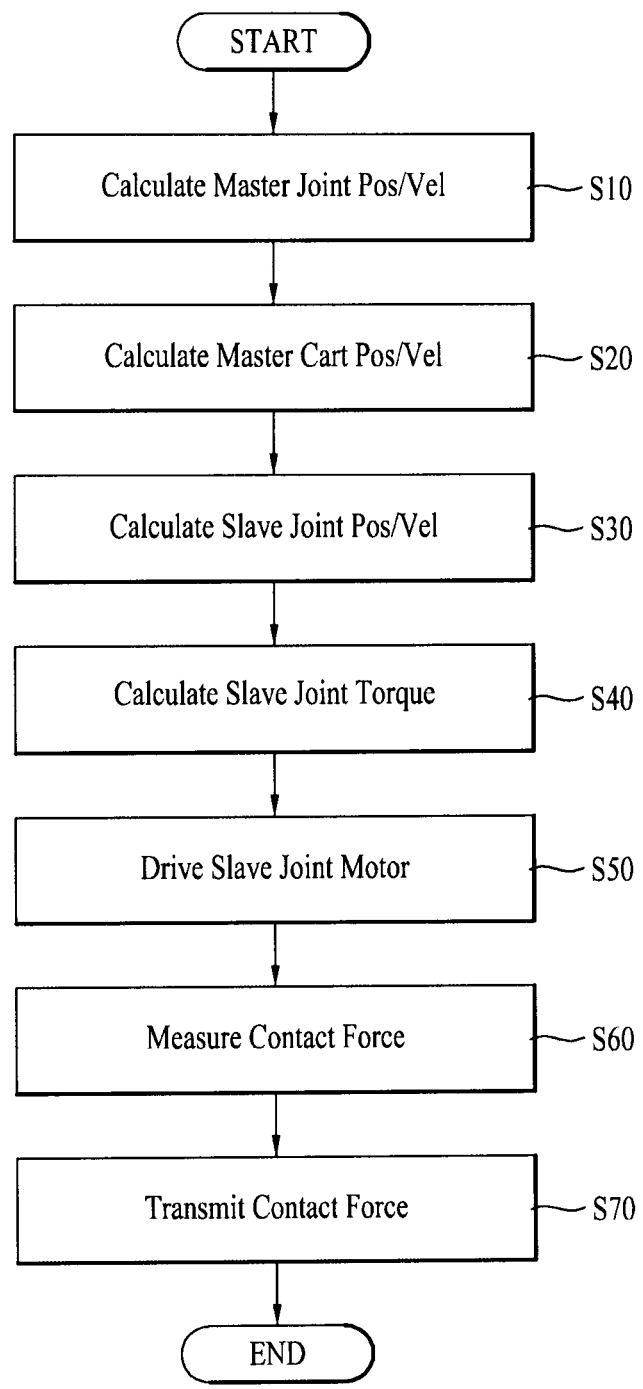
FIG. 10 is a flow chart illustrating a method of controlling a medical robotic system according to an exemplary embodiment of the present invention.

FIG. 10 shows a flow chart of the method according to the exemplary embodiment of the present invention. The method measures the contact force due to the contact between a surgical instrument (i.e. end effector) and tissue or an organ of a patient during a surgical procedure using the medical robotic system, and transmit the measured force to an input device of the medical robotic system.

In S10, master joint positions and velocities are calculated.
In S20, master joint positions and velocities are received, and transformed into Cartesian positions and velocities, using, for example, a Jacobian matrix.

In S30, the Cartesian positions and velocities are received and transformed into slave joint positions and velocities.

In S40, the slave joint positions and velocities are received and slave joint torque signals for the slave joint motors are generated based on the slave joint positions and velocities.

In S50, the slave joint torque signals are received, electric currents corresponding to the slave joint torque signals are generated, and the electric currents are supplied to the corresponding slave joint motors. Slave joint currents are also measured. For example, the current may be measured by monitoring a current feedback signal of a drive circuit of a DC brush motor. As another example, in case of a BLDC motor, the current may also be measured by monitoring a current feedback signal, where the current feedback signal is generated by removing phase sinusoidal components from a current signal for driving the motor, and the current signal is output from a drive circuit where the current signal is synchronized with a phase output signal having a sinusoidal form for improving electrical cogging characteristics.

In S60, the slave joint currents, the slave joint positions and velocities, and a contact signal are received and size and direction of a contact force caused by the contact of the surgical instrument to tissue are calculated based on the slave joint currents, the slave joint positions and the slave joint velocities measured when the contact is occurred and measured when the contact is not occurred, where the contact force may be a Cartesian force/movement 1. However, the present invention is not limited to this, and the contact force may also be a contact force in a joint space. Further details for the step S60 will be described in reference to FIG. 11 and FIG. 12.

In S70, the Cartesian force/movement is received, a corresponding torque signal in joint space is generated using, for example, the Jacobian transpose matrix, the master torque signals is received, electric currents corresponding to the master torque signals are generated, and the electrical currents are supplied to corresponding master joint motors in the input device. As a result, a surgeon operating the input device feels the contact force when the surgeon instruments and the tissue are contacted with each other.

Figure 11:
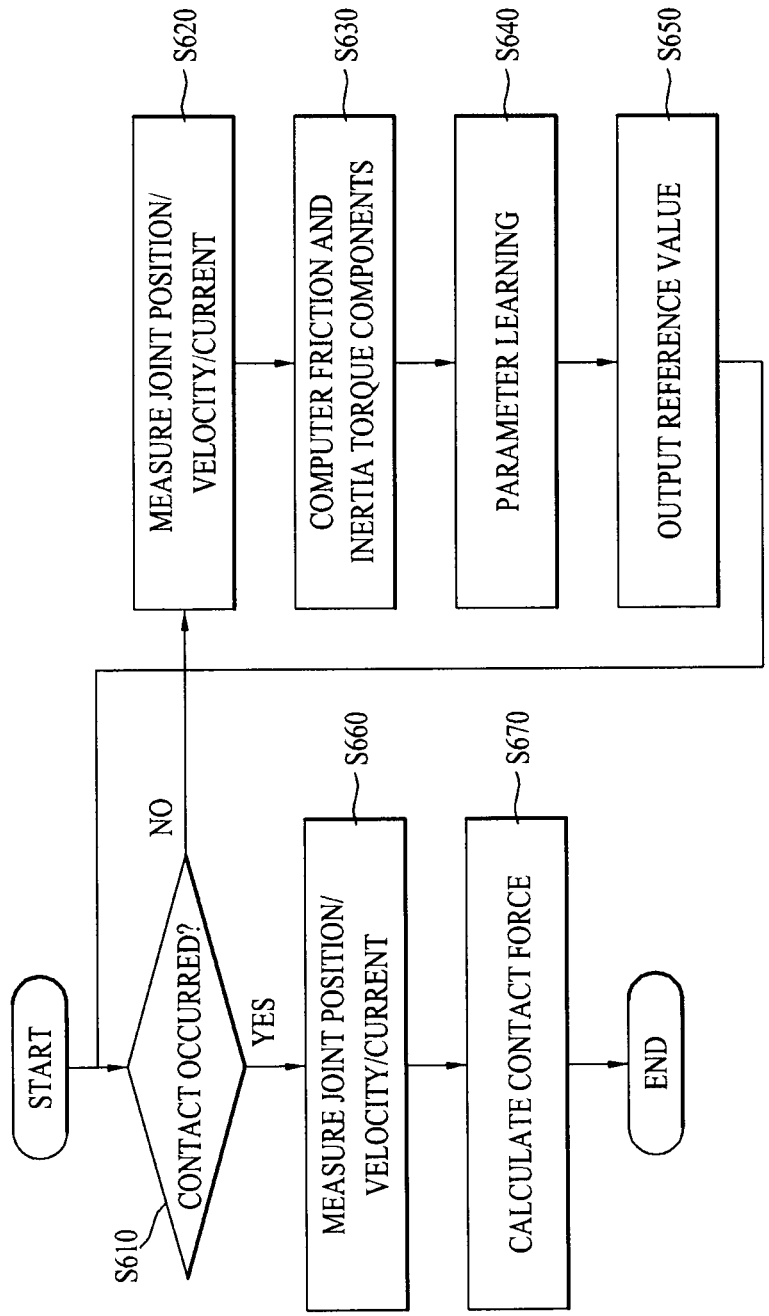
FIG. 11 is a flow chart illustrating a method of measuring contact force according to the exemplary embodiment of the present invention.

FIG. 11 shows a flow chart illustrating a method of measuring the contact force according to an exemplary embodiment of the present invention.

In S610, it is determined whether the surgical instrument is contacted with tissue of a patient or not. In this case, the contact between the end effector and the tissue may be detected by measuring a leakage current generated when the contact is occurred (FIG. 7), and the contact may be detected by measuring discharge induced by the contact (FIG. 8). In addition, the contact may be detected by using a plurality of separate electrodes located respective portions of the end effector such that a portion of the end effector at which a contact is occurred can be determined (FIG. 9).

In this case, the contact signals may include high frequency distortion due to various noises, thereby the signals may be maintained as a contact status once a contact is detected even though the signal is distorted during a certain period, and the period of the maintenance may be initialized when a contact is detected again.

In S620, a joint velocity, a joint position and a joint current when the surgical instrument is not contacted with the tissue are measured. For example, the joint position (i.e. angle) and the joint velocity (i.e. angular velocity) may be measured by using an incremental encoder. The incremental encoder may be attached to an axis of a slave joint motor, its value is initialized at a predetermined position, and the joint position is measured by the change of the value of the encoder with respect to the initialized value. The joint velocity is calculated by measuring the change of the value during a predetermined time interval. As another example, the joint position and velocity may be measured by using an analog potentiometer of which resistance is changed according to the angle of rotation and a tachometer of which voltage is changed according to the velocity of the rotation. The joint position is measured by supplying a reference voltage to the analog potentiometer and detecting the output voltage according to the change of the resistance. The joint velocity is measured by detecting the output voltage of the tachometer.

The current may be measured by monitoring a current feedback signal of a drive circuit of a DC brush motor. As another example, in case of a BLDC motor, the current may also be measured by monitoring a current feedback signal, where the current feedback signal is generated by removing phase sinusoidal components from a current signal for driving the motor, and the current signal is output from a drive circuit where the current signal is synchronized with a phase output signal having a sinusoidal form for improving electrical cogging characteristics.

In S630, the joint position and the joint velocity are received, the Cartesian force/moment, and torque components generated by friction and inertia of the joint motor are computed based on the joint position, the joint velocity and the Cartesian force/moment when the contact is not occurred.

In S640, the current/torque conversion constant, the rotor inertia constant and the friction constant are stored when the contact is not occurred. Initial values of the constants which are derived from additional experiments may be stored in a memory, and certain ranges of the constants may only be learned in order to improve the stabilization of the learning.

In S650, the contact signal is received, and a reference value for the contact force is output when the contact is not occurred. The method then loops back to S610 to continue to determine whether the contact is occurred or not.

In S660, a joint velocity, a joint position and a joint current when the surgical instrument is contacted with the tissue are measured. The examples for measuring the joint position, velocity and current explained in S620 may also be adapted to this step.

In S70, the slave joint currents, the slave joint positions and velocities, and a contact signal are received, and size and direction of a contact force caused by the contact of the surgical instrument to tissue are calculated based on the slave joint currents, the slave joint positions and the slave joint velocities, where the contact force may be a Cartesian force/movement. Further details for S70 will be described in reference to FIG. 12.

Figure 12:
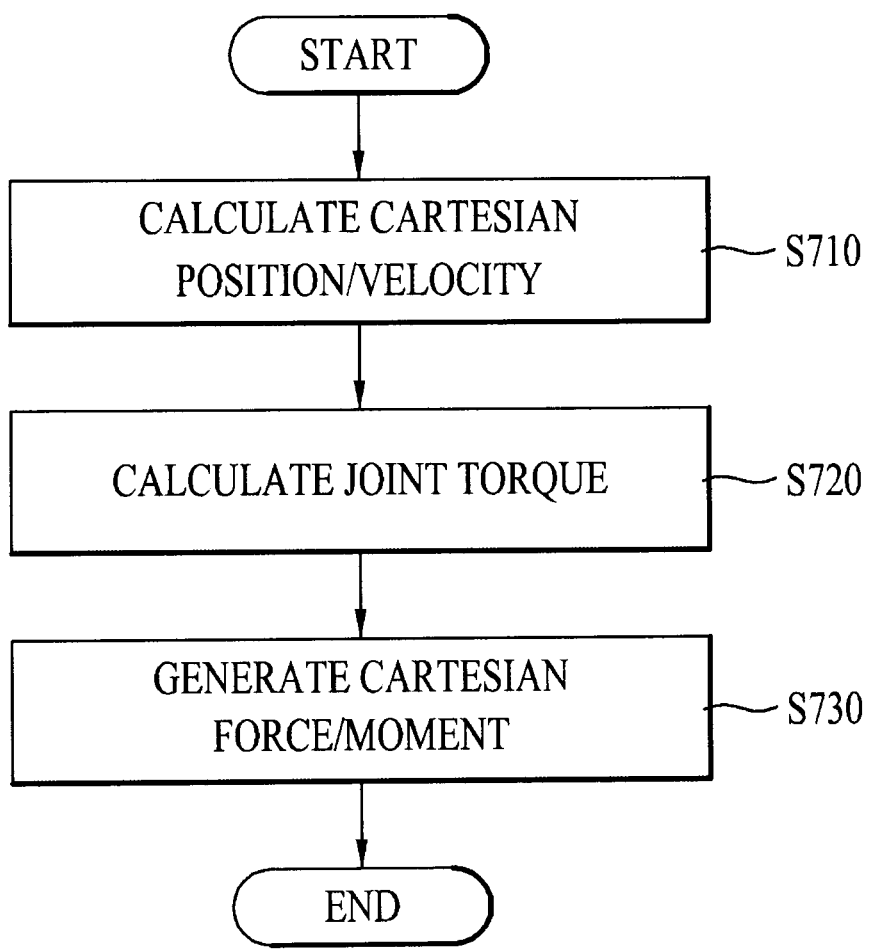
FIG. 12 is a flow chart illustrating a method of calculating a contact force according to the exemplary embodiment of the present invention.

FIG. 12 shows a method of calculating the contact force according to the exemplary embodiment of the present invention.

In S710, the joint position and the joint velocity are received and converted a Cartesian position and a Cartesian velocity respectively in a Cartesian space which is set up based on a screen (i.e. obtained through a laparoscope).

In S720, the joint currents are received and converted into joint torque signals. In more detail, a time domain response of the joint torque signal considering rotor inertia and friction of the joint motor is calculated by using a motor model, wherein the motor model may be represented by the following formula:

$$\text{Torque} = JM\frac{d^2 i}{dt^2} + KM(i) - sat(vel/\eta)FM$$

where "JM" is a rotor inertia constant, "KM" is a current/torque conversion constant, "vel" is a joint velocity, "$\eta$" is a chattering removal margin, "sat( )" is a saturation function, and "FM" is a friction constant.

In S730, the joint torque signals are received, the Cartesian position and the Cartesian velocity are received, and Cartesian force/moment of the contact force are generated based on the joint torque signal and the Cartesian position/velocity, using, for example, a Jacobian matrix.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A medical robotic system comprising:
   an input device;
   a robotic arm assembly;
   a surgical instrument operably coupled to the robotic arm assembly, the surgical instrument including a contact detection unit configured to detect a contact of the surgical instrument with tissue of a patient;
   a current measurement unit configured to measure a joint current in the robotic arm assembly;
   a position/velocity measurement unit configured to measure a joint position and a joint velocity in the robotic arm assembly;
   an external force calculation unit configured to calculate size and direction of a contact force caused by the contact of the surgical instrument to the tissue based on the joint currents, the joint positions and the joint velocities measured when the contact is occurred and measured when the contact is not occurred,
   wherein the external force calculation unit calculates the size and direction of a contact force based on a time domain response of a joint torque signal considering rotor inertia and friction of a joint motor by using a motor model, and
   wherein the motor model is represented by the following formula:

$$\text{Torque} = JM\frac{d^2 i}{dt^2} + KM(i) - sat(vel/\eta)FM,$$

where "JM" is a rotor inertia constant, "KM(i)" is a current/torque conversion constant, "vel" is a joint velocity, "$\eta$" is a margin value for removing chattering, "sat( )" is a saturation function, and "FM" is a friction constant.

2. The medical robotic system of claim 1, wherein the external force calculation unit includes an output unit configured to,
- receive a contact signal from the contact detection unit,
- output the contact force when the contact is occurred, and
- output a reference value for the contact force when the contact is not occurred.

3. The medical robotic system of claim 2, wherein the external force calculation unit includes,
- a coordinate calculation unit configured to receive the joint position and the joint velocity from the position/velocity measurement unit and convert the joint position and the joint velocity into a Cartesian position and a Cartesian velocity respectively,
- a joint motor simulation unit configured to receive the joint current from the current measurement unit and convert the joint current into the joint torque signal, and
- a force/moment calculation unit configured to,
  - receive the joint torque signal from the joint motor simulation unit,
  - receive the Cartesian position and the Cartesian velocity from the coordinate calculation unit, and
  - generate Cartesian force/moment of the contact force based on the joint torque signal and the Cartesian position/velocity.

4. The medical robotic system of claim 3, wherein the joint motor simulation unit further comprises:
- a slave inverse dynamics unit configured to:
  - receive the joint position and the joint velocity from the position/velocity measurement unit,
  - receive the Cartesian force/moment as a feedback signal, and
  - compute torque components generated by friction and inertia of the joint motor based on the joint position, the joint velocity and the Cartesian force/moment when the contact is not occurred, and
- a parameter learning unit configured to store the current/torque conversion constant, the rotor inertia constant and the friction constant when the contact is not occurred.

5. The medical robotic system of claim 1, wherein the surgical instrument has an end effector including the contact detection unit, and the contact detection unit is located at the end effector and configured to detect a contact between the end effector and the tissue.

6. The medical robotic system of claim 5, wherein the contact detection unit is configured to detect the contact between the end effector and the tissue by measuring a leakage current generated when the contact is occurred.

7. The medical robotic system of claim 5, wherein the contact detection unit is configured to detect the contact between the end effector and the tissue by measuring discharge induced by the contact.

8. The medical robotic system of claim 5, wherein the contact measurement unit includes a plurality of separate electrodes located on respective portions of the end effector such that a portion of the end effector at which a contact is occurred can be determined.

9. The medical robotic system of claim 1, wherein the input device is configured to receive the contact force.

* * * * *